United States Patent
Nagu et al.

(10) Patent No.: US 10,858,742 B2
(45) Date of Patent: Dec. 8, 2020

(54) NITROGEN SUBSTITUTED AROMATIC TRIAZOLES AS CORROSION CONTROL AGENTS

(71) Applicant: General Electric Company, Schenectady, NY (US)

(72) Inventors: Muthukumar Nagu, Bangalore (IN); Amutha Nagarajan, Bangalore (IN); Paul Robert Frail, Trevose, PA (US); Edward Joseph Urankar, Trevose, PA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/095,156

(22) PCT Filed: May 10, 2017

(86) PCT No.: PCT/US2017/032042
§ 371 (c)(1),
(2) Date: Oct. 19, 2018

(87) PCT Pub. No.: WO2017/197047
PCT Pub. Date: Nov. 16, 2017

(65) Prior Publication Data
US 2019/0127859 A1    May 2, 2019

(30) Foreign Application Priority Data

May 10, 2016  (IN) .............................. 201641016305

(51) Int. Cl.
| | | |
|---|---|---|
| C23F 11/14 | (2006.01) | |
| C23F 11/10 | (2006.01) | |
| C23F 11/08 | (2006.01) | |
| C02F 5/12 | (2006.01) | |
| C07D 249/18 | (2006.01) | |
| C02F 103/02 | (2006.01) | |

(52) U.S. Cl.
CPC ............ *C23F 11/149* (2013.01); *C02F 5/125* (2013.01); *C07D 249/18* (2013.01); *C23F 11/08* (2013.01); *C23F 11/10* (2013.01); *C02F 2103/023* (2013.01); *C02F 2303/08* (2013.01)

(58) Field of Classification Search
CPC ......... C23F 11/149; C23F 11/08; C23F 11/10; C07D 249/18; C02F 5/125; C02F 2103/023; C02F 2303/08
See application file for complete search history.

(56) References Cited

U.S. PATENT DOCUMENTS

| | | | |
|---|---|---|---|
| 4,184,991 A * | 1/1980 | Scheurman, III | ....... C23F 11/10 106/14.16 |
| 5,772,919 A | 6/1998 | Reichgott et al. | |
| 2009/0173910 A1 | 7/2009 | Hirano et al. | |

FOREIGN PATENT DOCUMENTS

| | | | |
|---|---|---|---|
| CN | 103992284 A | | 8/2014 |
| JP | 2009283751 A | * | 12/2009 |
| JP | 2012031501 A | | 2/2012 |

OTHER PUBLICATIONS

English Translation of JP 2009283751 (Year: 2009).*
Hollander O., et al., "The Chemistry of Azole Copper Corrosion Inhibitors in Cooling Water." Corrosion, Nace, vol. 41, No. 1, Jan. 1, 1985, pp. 39-45.
International Search Report for Appl. No. PCT/US2017/032042 dated Nov. 16, 2017, pp. 1-4.

* cited by examiner

*Primary Examiner* — Andrew J. Oyer
(74) *Attorney, Agent, or Firm* — Wegman Hessler

(57) ABSTRACT

Compositions and methods for inhibiting corrosion of metallic surfaces in contact with an aqueous medium such as copper, copper alloy, and steel surfaces of an open recirculating cooling water system. In certain embodiments, an aromatic triazole having an anionic substituent bonded to a nitrogen atom of the triazole (ANST) is used as the corrosion inhibitor. In other embodiments, the corrosion inhibitor is a reaction product of an aromatic triazole and an aldehyde (ATA).

6 Claims, No Drawings

NITROGEN SUBSTITUTED AROMATIC TRIAZOLES AS CORROSION CONTROL AGENTS

CROSS-REFERENCE TO RELATED APPLICATIONS

This application claims priority to PCT Appl. Serial No. PCT/US2017/032042, filed May 10, 2017, which claims the benefit of Indian Application Serial No. 201641016305, filed May 10, 2016, the entireties of which are incorporated herein by reference.

BACKGROUND OF THE INVENTION

In many industrial processes, undesirable heat is removed by the use of heat exchangers in which water is used as the heat exchange medium. Copper and copper bearing alloys are often used in the fabrication of such heat exchangers as well as in other parts in contact with the cooling water such as pump impellers, stators, and valve parts.

The cooling water systems most often used are of the recirculating type where the water is used repetitively and, as a result, remains in extended contact with the metals of the cooling water system. The cooling water is often corrosive towards these metals given the ions present and the intentional introduction of oxidizing substances for biological growth control. In refinery operations, these cooling waters are often contaminated by "sour" leaks which result in hydrocarbons, sulfides, polysulfides, and hydrogen sulfide being present in the cooling water.

These contaminants can become problematic if they are left untreated and can quickly overwhelm any standard operating treatment. The hydrocarbons can coat the metal surfaces of the cooling system and prevent corrosion inhibitors from working correctly. Sulfide ions can cause severe corrosion of metals and are particularly corrosive of copper and its alloys, such as brass and admiralty metal.

Hydrogen sulfide will penetrate copper metallurgy and will form cupric sulfide. The consequences of such corrosion are the loss of metal from the equipment, leading to failure or requiring expensive maintenance, creation of insoluble corrosion product films on the heat exchange surfaces leading to decreased heat transfer and subsequent loss of productivity. Discharge of copper ions can result in them "plating out" on less noble metal surfaces, such as iron, and cause severe galvanic corrosion. Copper discharge is also a health and environmental concern due to its toxicity.

Steel corrosion is a degradative electrochemical reaction of the metal with its environment. Simply stated, it is the reversion of refined metals to their natural state. For instance, iron ore is iron oxide which is refined into steel. Corrosion of the steel results in the formation of iron oxide which, if left unattended, may result in failure or even destruction of the metal.

SUMMARY OF THE INVENTION

In one embodiment, the invention relates to compositions and methods for inhibiting corrosion of metals in contact with aqueous systems using aromatic triazole compounds having anionic substituents bonded to a nitrogen atom or atoms of the triazole moiety.

In one exemplary embodiment of the invention, compositions are provided that comprise an aromatic triazole having an anionic substituent bonded to a nitrogen atom of the triazole (ANST). In some embodiments, the ANST is represented by the formula

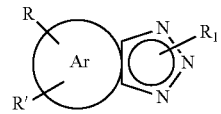

Formula I(a)

wherein R and R' are each independently H, OH, $CO_2H$, $C_1$-$C_6$ alkyl, $C_1$-$C_6$ alkoxy, halo, $SO_3H$, $SO_3M$, $R_2SO_3H$, or $R_2SO_3M$, wherein $R_2$ is a $C_1$-$C_6$ alkyl group and M is an alkali metal or alkaline earth metal, Ar is an aromatic group, $R_1$ is an anionic moiety.

Further, in certain embodiments, $R_1$ is phosphate, sulfate, sulfonate, phosphonate, or carboxy group or alkali metal or alkaline earth metal salts thereof or $R_1$ is —$R_3Z_{(n)}$ wherein n is an integer of 1 or greater, each Z is independently chosen from carboxy, phosphate, sulfate, sulfonate, phosphonate, or alkali metal or alkaline earth metal salts thereof, and $R_3$ is $C_1$-$C_6$ alkyl, $C_1$-$C_6$ alkoxy, or $C_1$-$C_6$ hydroxylated alkyl.

In certain exemplary embodiments, the ANST compositions have the formula

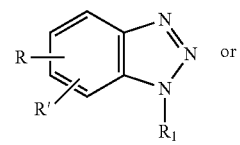

Formula II(a)

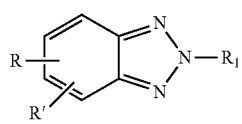

Formula II(b)

or mixtures of Formulae II(a) and II(b).

In some examples, R and R' are both H or R is H and R' is methyl.

In other embodiments, $R_1$ is COOH, $SO_3H$, or $R_3Z_{(n)}$ wherein $R_3$ is $CH_2$, Z is COOH and n=1; $R_3$ is —$CH_2CH_2$— and Z is COOH, n=2; $R_3$ is $C_1$-$C_6$ hydroxylated alkyl, Z=sulfonate and n=1; or $R_3$ is $CH_2$, Z is phosphonate and n=1.

In other embodiments, $R_1$ is $R_3Z_{(n)}$, $R_3$ is 2-hydroxylpropyl, or 1-hydroxypropyl, and Z is sulfonate and n=1.

In further embodiments, $R_1$ is $R_3Z_{(n)}$, $R_3$ is $CH_2$, Z is phosphonate and n=1.

In further embodiments, $R_1$ is COOH. Other exemplary embodiments include an ANST of Formula I(a) or II(b) wherein $R_1$ is $R_3Z_{(n)}$, $R_3$ is $CH_2$, Z is carboxy and n is 1. Still other embodiments include ANST compounds wherein $R_1$ is $R_3Z_{(n)}$, $R_3$ is —$CH_2$—$CH_2$, Z is carboxy and n is 2, and in further embodiments, $R_1$ is $SO_3H$.

Methods are also disclosed for inhibiting corrosion metal surfaces in contact with an aqueous medium comprising adding to the aqueous medium an ANST as set forth above. In certain embodiments, the cooling water system is an open recirculating cooling water system, and the ANST is added to the cooling water system in an amount of about 0.1-100 ppm. In certain exemplary embodiments, the metal surfaces in contact with the cooling water system comprise copper, copper alloy or steel metallurgies. In other embodiments, corrosion inhibition is obtained by providing for the formation of a protective oxide film on metal surfaces. The method further comprises the steps of adding orthophosphate and water soluble polymer, in addition to the ANST, to the aqueous medium. In some cases, the water may have sufficient orthophosphate content so additional orthophosphates need not be added. ANSTs may be used in the presence of other commercial azoles, benzotriazole, tolyltriazole, and their respective alkyl and halogenated derivatives, to further improve their corrosion protection performance.

In other embodiments of the invention, methods are provided for inhibiting corrosion of metal surfaces in contact with an aqueous medium comprising adding to the aqueous medium a reaction product of an aromatic triazole and an aldehyde (hereinafter ATA). In certain embodiments, the aromatic triazole is present in an amount of about 0.1-2.0 moles per mole of the aldehyde.

In further embodiments, from about 0.1-100 ppm of the ATA is added to the aqueous medium based upon one million parts of the aqueous medium and in further embodiments, the aqueous medium comprises an open recirculating cooling water system, and the metallurgy may comprise copper, copper alloy, or steel surfaces.

In further embodiments, the aromatic triazole is selected from the group consisting of benzotriazole, tolyltriazole, and chlorobenzotriazole. The aldehyde may, for example, be chosen from the group consisting of paraformaldehyde, formaldehyde, acetaldehyde, glyoxal, and glyoxylic acid. In certain embodiments, the ATA is utilized to help form a protective oxide film along the system metallurgy in contact with the aqueous medium. In these cases, orthophosphate may be added, or may be present in the system, and a water soluble polymer may also be added to the aqueous medium. ATAs may be used in the presence of other commercial azoles, benzotriazole, tolyltriazole, and their respective alkyl and halogenated derivatives, to further improve their corrosion protection performance.

DETAILED DESCRIPTION

In certain embodiments of the invention, aromatic triazole compounds having anionic substituents bonded to triazole nitrogen atoms are disclosed. These compounds are useful as corrosion inhibitors for copper, stainless steel, and Fe based metallurgies that are in contact with aqueous systems such as cooling water systems, heat exchange systems, closed loop systems, wastewater systems, pulping process systems, boiler and other steam generating systems, papermaking processes, coke oven gas systems, food and beverage processing systems, gas scrubbing systems, paint detackification systems, automotive and tire washing systems, reverse osmosis, and membrane systems, etc.

In other embodiments, the N-anionic substituted aromatic triazole compounds (ANST) have the formula

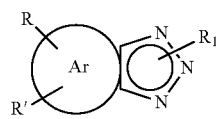

Formula I(a)

wherein R and R' are each independently H, OH, $CO_2H$, $CO_2M$, $C_1$-$C_6$ alkyl, $C_1$-$C_6$ alkoxy, halo, $SO_3H$, $SO_3M$, $R_2SO_3H$, or $R_2SO_3M$, wherein $R_2$ is a $C_1$-$C_6$ alkyl group and M is an alkali metal or alkaline earth metal, Ar is an aromatic group such as benzene, napthalene, anthracene, etc. $R_1$ is an anionic moiety.

In some embodiments, $R_1$ is phosphate, sulfate, sulfonate, phosphonate, or carboxy or alkali metal or alkaline earth metal salts thereof, or $R_1$ is —$R_3Z(n)$ wherein n is an integer of 1 or greater, each Z is chosen independently from carboxy, phosphate, sulfate, sulfonate, phosphonate or alkal metal or alkaline earth metal salts thereof, and $R_3$ is $C_1$-$C_6$ alkyl, $C_1$-$C_6$ alkoxy, or $C_1$-$C_6$ hydroxylated alkyl.

In some embodiments, Ar is a benzene ring with both R and R' being H. The molecule is an N-substituted benzotriazole. When either R or $R_1$ is $CH_3$ with the other being H, the resulting molecule is N-substituted tolyltriazole. In some embodiments, $R_1$ is not carboxy or phosphonate, and in some embodiments, Z is not phosphonate.

In other aspects of the invention, the anionic N-substituted triazole compounds (ANST) have an anionic moiety located at either the 1 or 2 nitrogen atom of the triazole ring. By the term anionic moiety, we mean that a negatively charged functional group is either directly covalently bonded to one of the triazole N atoms or the negatively charged functional group may be a substituent on an alkyl, hydroxyalkyl, or alkoxyl group that is itself covalently bonded to one of the triazole N atoms. The negative charge can be generated by changes in pH depending on the functional group's pKa: strong acid groups will have a large percentage of negative charge over a wide pH range, and weak acid groups will have a larger percentage of negative charge near neutral pH and higher concentration as pH increases toward alkaline.

In some aspects of the invention, the ANSTs are mixtures wherein the anionic moiety is positioned at the 1-nitrogen position in some compounds of the mixture and the anionic moiety is positioned at the number 2 nitrogen position in other compounds of the mixture.

A host of exemplary negatively charged functional groups can be employed as a triazole nitrogen substituent. For example, in various aspects of the invention, the anionic functionality can be selected from the following groups:
  i) phosphate
  ii) phosphonates
  iii) sulfates
  iv) sulfonates
  v) carboxylates, etc.

In one aspect of the invention, the ANST is a benzotriazole compound having the Formulae II(a) and II(b) or the ANST is a mixture of compounds of Formulae II(a) and II(b) wherein

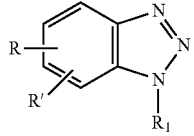

Formula II(a)

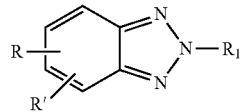

Formula II(b)

with R, R', and $R_1$ are independently chosen and are as defined in conjunction with Formula I(a) above.

In another aspect of the invention, the ANST is chosen in accordance with Formulae II(a) or II(b) wherein R and R' are both H (benzotriazole) or one of R and R' is H with the other of R and R' being $CH_3$ (tolyltriazole). In other cases, R is $SO_3M$ and R' is a $C_1$ to $C_6$ alkyl group such as a methyl group. In some exemplary embodiments, $R_1$ is COOH, or $SO_3H$. In other embodiments, $R_1$ is $R_3$ Z(n) wherein a) $R_3$ is $CH_2$ and Z is COOH, n=1; b) $R_3$ is —$CH_2$—$CH_2$—; and Z is COOH, n=2; c) $R_3$ is hydroxylated alkyl, Z=sulfonate and n=1; d) $R_3$ is $CH_2$ and Z is phosphonate and n=1.

In one embodiment of the invention, an ANST or mixture thereof is added to a water system such as a cooling water system to inhibit corrosion of metals in contact with the system water. Exemplary metals for which corrosion inhibition is required may include copper based metallurgies such as admiralty brass, or low carbon steel, stainless steel, etc. Generally, the anionically charged functional groups provide: enhanced water solubility across a broad pH spectrum, improved surface bonding capacity, improved chlorine stability, improved chelation capabilities, and improved corrosion protection.

In another embodiment, the ANSTs serve as corrosion inhibitors, even in those aqueous systems, such as cooling water systems, in which oxidizing substances are present in order to inhibit microbial growth. For example, the ANSTs may be advantageously utilized in systems containing chlorine-containing oxidants, such as, for example, chlorine, chlorine dioxide, sodium chlorite, hypochlorous acid, hypochlorites (e.g., sodium hypochlorite, calcium hypochlorite, etc.), chlorine bleach, etc., nonchlorine-containing oxidants such as acids (e.g., sulfuric acid, nitric acid, etc.), caustics, (e.g., sodium hydroxide, potassium hydroxide, etc.), non-chlorine bleach peroxides (e.g., hydrogen peroxide, sodium peroxide, etc.), ozone, etc.

In other embodiments, the ANST may be employed in aqueous systems in which the metallurgy in contact with the system water is treated to provide a protective or passivated film on the metal surface. In such cases, the passivation of iron based metallurgies is typically accomplished through the formation of a cathodic inhibiting calcium phosphate film. Anionic molecules or polymers act as either inhibitors or dispersants of calcium phosphate scale and allow a controlled deposited calcium phosphate film for corrosion control. This deposited film has no negative impacts on industrial assets that rely on heat transfer such as heat exchangers in cooling systems. The anionic functional groups on the ANST can facilitate the formation of calcium phosphate inhibiting films on various metallurgies (this includes the various mixed alloys such as admiralty, stainless steel, etc.) including copper, iron, aluminum, etc. The passivating film thus consists of a mixture of inorganic salt and ANST on top of a metal oxide layer versus just an azole mechanism. In aggressive waters (grey and or reuse water, high cycle water, RO reject, etc.) that feature increases in conductivity, chlorides, sulfates, TSS total suspended solids, TDS (total dissolved solids), ammonia, oxidizing biocides such a mechanism is desired and forms a more robust field at a much lower dose than typical azoles. Proper passivation of a metal surface will result in decrease metal throw into the aqueous industrial stream.

In some systems adapted to provide passivated films, a treatment comprising an orthophosphate constituent and water soluble polymer is added to system waters that have a calcium ion concentration in excess of about 15 ppm and a pH of about 6.5-9.5. Orthophosphate concentration is on the order of about 6-30 ppm. Typical orthophosphate constituents include phosphoric acid, the sodium orthophosphates, potassium orthophosphates, lithium orthophosphates and ammonium orthophosphates. Also, organic orthophosphates such as those set forth in U.S. Pat. No. 3,510,436 can be mentioned as effective.

The polymers that may be used in order to promote the protective film may include water soluble copolymers or terpolymers based on acrylic acid/hydroxylated alkyl acrylate esters, particularly acryl acid/2 hydroxypropylacrylate copolymers and its salts. Other exemplary copolymers may comprise acrylic/acid/allyl hydroxyalkylsulfonate ether polymers such as acrylic acid/allyhydroxypropyl sulfonate ether. In most cases, the orthophosphate component is added in an amount of about 1-30 ppm based on one million parts of the system water. The polymer is present in an amount of about 1-50 ppm, and the ANST may be present in an amount of about 1-50 ppm. Techniques pertaining to formation of passivated film may be seen upon review of U.S. Pat. No. 4,303,568.

In other exemplary embodiments, the invention pertains to a process for treating copper based alloys in contact with the aqueous medium of an open cooling system. In some embodiments, a process is provided in which from about 0.1-100 parts by weight of the ANST is provided, for every 1 million parts by weight of the aqueous medium. In other embodiments, from about 1-50 ppm may be added with other embodiments adding from 3-5 ppm.

The invention will be highlighted in the following illustrative examples which should not be viewed to limit or narrowly construe the invention.

EXAMPLES—SET I

Example 1—Beaker Corrosion Testing

A test water as shown in Table A was poured into test beakers. The beakers consisted of a standard 3-electrode electrochemical set up with reference, counter, and working electrodes. The reference and counter electrodes were composed of Hastelalloy $C_{22}$ (UNS N06022) stainless steel alloy, and the working electrode was admiralty brass. The working electrode was polished with 600 grit paper and a lathe in order to expose a fresh metal surface prior to testing. The synthetic water shown in Table A was made from stock solutions of $CaCl_2$, $MgSO_3$, $NaHPO_4$, $NaHCO_3$, sulfonated polycarboxylic acid terpolymer, and N-substituted azole diluted in DI water.

Beaker volume was 1.9 L. Prior to starting the corrosion experiment, beakers were equilibrated in water bath set 120° F. and vigorously stirred at 400 rpm with air/$CO_2$ continuous sparging to maintain pH. The corrosion experiment and data collection were done using a PAR 273A and computer. Bleach experiments allowed azole treatments to form a film on the working electrode and then a onetime shot dose of 5 ppm bleach was added to the beakers. At the end of each experiment, electrodes were photographed and water samples taken for analysis. Corrosion rates for beaker experiments were determined as an average of all instantaneous values calculated from the linear polarization method with data acquisition taken between every 1-2 hours for ~40 hours. 3 ppm of azole or comparative treatment were used in every test.

TABLE A

|  |  | Units | Neutral | Alkaline |
|---|---|---|---|---|
| pH | | pH | 7.2 | 8.6 |
| Polymer | | ppm | 2-8 | 8 |

TABLE A-continued

|  | Units | Neutral | Alkaline |
|---|---|---|---|
| Ca | ppm as $CaCO_3$ | 600 | 400 |
| Mg | ppm as $CaCO_3$ | 300 | 150 |
| $oPO_4$ | ppm | 15 | 6 |
| M-alk | ppm | 50 | 250 |
| Chlorides | ppm | 425-1425 | 283 |
| Sulfates | ppm | 288 | 144 |
| FRC | ppm | 0.2-1.0 | 0.2 |

The results of the beaker test are shown in Table I.

TABLE I

Beaker Testing

|  | Anionic Azole Substituent | Substituent Position on BZT Triazole Ring | Corrosion Rate (mpy) no bleach | Corrosion Rate (mpy) with bleach |
|---|---|---|---|---|
| X-1 | COOH | 1 | 0.03 | 0.62 |
| X-2 | $CH_2COOH$ | mixture of 1, 2 | 0.03 | 0.58 |
| X-3 | $COOHCH_2CH_2COOH$ | mixture of 1, 2 | 0.01 | 0.23 |
| X-4 | $SO_3H$ | 2 | 0.02 | 0.76 |
| X-5 | $CH_2CH(OH)CH_2SO_3H$ | mixture of 1, 2 | — | 0.77 |
| X-6 | $CH_2PO_3H$ | Reaction Prod. | 0.03 | 0.52 |
| C-1 | Benzotriazole |  | 0.01 | 1.64 |

BZT refers to benzotriazole.

Some non-charged N-substituted azole compounds and some hydrophobic N-substituted compounds were also tested but were eliminated from further consideration due to either their lack of efficacy in the bleach containing tests or their hydrophobicity.

Example 2—Recirculator Testing

A recirculating testing rig was provided. The rig had a total volume of ~1.4 L and was equipped with a sump pump, by-pass rack for corrosion coupons and probes, Plexiglas encased heat exchanger, and probes to control pH and ORP. The water chemistry was as shown in Table A above. The heat exchanger was fitted with an electrical heater to control heat load, 0-11,000 BTU/ft2/hr, and flow meters, 0-4.6 ft/sec. Corrosion rates were monitored using 2-probe instantaneous meters fitted in the by-pass rack. Weight loss corrosion rates were calculated by inserting coupons into the bypass rack for the duration of the testing period, 7-8 days. The pH was controlled using a sulfuric acid drip. Oxidation Reduction Potential (ORP) was controlled to the desired Free Residual Chlorine (FRC) level as determined by the Hach powder pack method. Water flow was maintained at ~4 ft/sec and bulk water temperature was controlled at 120° F. Results are shown in Table II.

TABLE II

BTU Testing

|  | Azole Moiety | Dose | Polymer ppm | pH | Ca ppm | $oPO_4$ | Chlorides ppm | FRC ppm | Cu coupon mpy | Cu probe mpy |
|---|---|---|---|---|---|---|---|---|---|---|
| C-1 | BZT | 2.00 | 2.00 | 7.20 | 600 | 15 | 425 | 0.20 | 0.45 | 0.14 |
| C-2 | TTA | 2.00 | 2.00 | 7.20 | 600 | 15 | 425 | 0.20 | 0.39 | 0.14 |
| X-2 | BZT-1-$CH_2COOH$ | 2.00 | 2.00 | 7.20 | 600 | 15 | 425 | 0.20 | 0.41 | 1.30 |
| X-14 | TTA-1-$CH_2$—COOH | 2.00 | 2.00 | 7.20 | 600 | 15 | 425 | 0.20 | 0.99 | 5.24 |
| X-4 | BZT-2-$SO_3H$ | 2.00 | 2.00 | 7.20 | 600 | 15 | 425 | 0.20 | 0.38 | 0.13 |
| C-1 | BZT | 2.00 | 8.00 | 8.60 | 400 | 6 | 283 | 0.20 | 0.41 | 0.06 |
| C-2 | TTA | 2.00 | 8.00 | 8.60 | 400 | 6 | 283 | 0.20 | 0.14 | 0.06 |
| X-2 | BZT-1-$CH_2COOH$ | 2.00 | 8.00 | 8.60 | 400 | 6 | 283 | 0.20 | 0.31 | 0.06 |
| X-14 | TTA-1-$CH_2COOH$ | 2.00 | 8.00 | 8.60 | 400 | 6 | 283 | 0.20 | 0.44 | 0.04 |
| X-4 | BZT-2-$SO_3H$ | 2.00 | 8.00 | 8.60 | 400 | 6 | 283 | 0.20 | 0.13 | 0.007 |
| C-1 | BZT | 3.00 | 8.00 | 7.20 | 600 | 15 | 1425 | 1.00 | 1.14 | 0.54 |
| C-2 | TTA | 3.00 | 8.00 | 7.20 | 600 | 15 | 1425 | 1.00 | 1.02 | 0.25 |
| X-5 | BZT-$CH_2CH(OH)CH_2SO_3H$ | 3.00 | 8.00 | 7.20 | 600 | 15 | 1425 | 1.00 | 0.72 | 0.46 |
| X-15 | TTA-$CH_2CH(OH)CH_2SO_3H$ | 3.00 | 8.00 | 7.20 | 600 | 15 | 1425 | 1.00 | 1.53 | 0.68 |

C-1 and C-2 are control.
BZT = benzotriazole
TTA = tolyltriazole

The compounds of one aspect of the invention, namely X-1 through X-6 and X-14 through X-15 are illustrative embodiments of the invention. Synthesis information for each is as follows:

(X-1) 1-COOHBZT—prepared via in situ hydrolysis of corresponding acid chloride. Calculated amount of 1 mole BZT, 2 moles triphosgene and THF were added to a round bottomed flask and allowed to stir for 72 hours. The excess product was evaporated and the solid product was acidified with HCl to pH3. The solid product was filtered and dried under vacuum.

(X-2) Benzozotriazole-1-acetic acid/Benzotriazole-2-acetic acid mixture: Reaction product of benzotriazole and chloroacetic acid.

Benzotriazole (11.9 g, 100 mmol) and Chloroacetic acid (9.45 g, 100 mmol) were dissolved in 60 mL of distilled water at room temperature. To the stirred solution 16.0 g of 50% aqueous sodium hydroxide solution was added. The reaction mixture was stirred dropwise for 5 hours during which time a white precipitate formed. The solid was filtered and washed with 20 ml of cold distilled water and dried to leave 7.2 g of white product.

(X-3) Reaction product of benzotriazole and maleic anhydride.

Benzotriazole (5.9 g, 50 mmol) and maleic anhydride (4.1 g, 42 mmol) were mixed within a flask while heating under a nitrogen atmosphere. A slight exotherm was evident as the reaction reached 50° C. and the solids dissolved. The solution was held at 80° C. for 6 hours and then was cooled to room temperature to provide 8.2 g of brown glassy solid.

(X-4) Benzozotriazole-2-sulfonic acid: Reaction product of benzotriazole and chlorosulfonic acid.

Benzotriazole (11.9 g, 100 mmol) was dissolved in 75 mL of tetrahydrofuran and cooled to 10° C. with an ice bath while stirring. Chlorosulfonic acid (12.2 g, 105 mmol) was added dropwise while keeping the temperature of the solution below 20° C. Upon completion of the addition, the solution was allowed to come to room temperature and is stirred overnight during which time a white solid precipitated. The solid was filtered and washed with 20 mL of cold THF and dried in vacuum to provide 6.9 g of product.

(X-5) Benzozotriazole-1-hydroxypropylsulfonate/Benzotriazole-2-hydroxypropylsulfonate: Reaction product of benzotriazole and 3-chloro-2-hydroxy-1-propanesulfonic acid sodium salt.

Benzotriazole (6.0 g, 50 mmol) and 3-chloro-2-hydroxy-1-propanesulfonic acid sodium salt hydrate (10.8 g, 55 mmol) were dissolved in 40 mL of distilled water at room temperature. To the stirred solution, 4.0 g of 50% aqueous sodium hydroxide solution was added dropwise, and the solution was heated to 60° C. for 6 hours. The solution was allowed to cool to room temperature, and the water was evaporated at reduced pressure. The resulting solid was washed with 30 mL of methanol and dried at room temperature to provide 15.0 g of white solid.

(X-6) Reaction product of benzotriazole, formaldehyde, and phosphorous acid.

Benzotriazole (11.9 g, 100 mmol) and phosphorous acid (9.84, 120 mmol) is dissolved in 100 ml of isopropanol at room temperature. To the solution is added 15.7 g (200 mmol) of 37% formaldehyde dropwise, which is stirred at room temperature for 1 hour followed by heating to reflux for 5 hours. The reaction is allowed to cool to room temperature and evaporated to dryness to leave 28.5 g of crude oil. The crude product was purified via column chromatography with silica gel 60 (particle size 35-70 μm, pore size 60 A) and dichloromethane/acetone gradient elution solvent to provide three reaction products after evaporation of the solvent. The first product to elute off the column was 13.65 g of a white solid identified as 1-(((propan-2-yl)oxy)methyl)-1H-benzotriazole followed by 4.5 g of white solid identified as benzotriazole-1-methanol. The third material isolated during the purification was 2.3 g of a clear oil identified as a reaction product of benzotriazole, formaldehyde, and phosphorus acid (X-6).

(X-14) Tolytriazole-1-acetic acid/Tolytriazole-2-acetic acid: Reaction product of Tolyltriazole and chloroacetic acid.

Tolyltriazole (13.3 g, 100 mmol) and Chloroacetic acid (11.34 g, 120 mmol) are dissolved in 70 mL of distilled water at room temperature. To the stirred solution is added 8.0 g of 50% aqueous sodium hydroxide solution dropwise. Stirring is continued for six hours during which time a white precipitate forms. The solid is filtered and washed with 20 ml of cold distilled water and dried to leave 4.7 g of white product.

(X-15) Tolytriazole-1-hydroxypropyl sulfonate/Tolytriazole-2-hydroxypropyl sulfonate: Reaction product of Tolyltriazole and 3-chloro-2-hydroxy-1-propanesulfonic acid sodium salt.

Tolyltriazole (26.63 g. 200 mmol) and 3-chloro-2-hydroxy-1-propanesulfonic acid sodium salt hydrate (43.25 g, 220 mmol) are dissolved in 160 mL of distilled water at room temperature. To the stirred solution is added 16.0 g of 50% aqueous sodium hydroxide solution dropwise, and the solution is heated to 45° C. for four hours and then held at 65° C. for six hours. The solution is allowed to cool to room temperature and 137 g of distilled water is added. The solution is determined to be 25.45% solids.

In another aspect of the invention, methods are provided for inhibiting corrosion of metal surfaces in an aqueous medium comprising adding to the medium a reaction product or products formed via reaction of an aromatic triazole and an aldehyde (ATA). For example, these ATA reaction products may comprise the reaction product of an aromatic triazole, such as benzotriazole, tolyltriazole, and the like with aldehydes such as paraformaldehyde, formaldehyde, acetaldehyde, glyoxal, or glyoxylic acid. In some embodiments, the aromatic triazole is present in the reaction medium in an amount of 0.1-2.0 moles per 1 mole of the aldehyde.

The reaction may proceed in a polar or non-polar medium including water, methanol, diethyl ether, etc. Acid catalysts may be employed. The ATA products formed via the reaction are characterized as having an alpha hydroxy moiety bonded to either the 1 N or 2 N position of the triazole ring. In some cases, mixtures of the 1 N alpha hydroxy moiety and 2 N alpha hydroxy moiety are present: alpha being counted from the triazole nitrogen ring.

General synthetic routes for exemplary ATAs are as follows:

Azole-Aldehyde—Synthesis

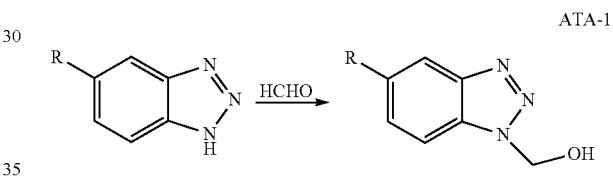

ATA-1

Procedure:

Azole was taken in required amount of methanol and heated to 65° C. Calculated amount of formaldehyde was added to the reaction mixture and continued to heat at 65° C. for four hours. The solid product was filtered and dried in vacuum.

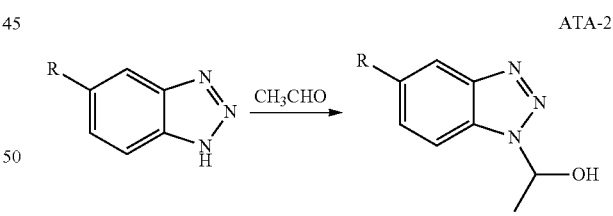

ATA-2

Procedure:

Azole and acetaldehyde were taken in diethyl ether, and the reaction mixture was kept at 25° C. for 12 hours. The reaction mass was filtered and solid product was washed with pentane and dried in vacuum.

Synthesis of Dibenzotriazole Glyoxal

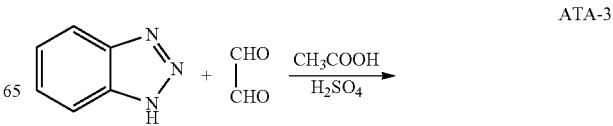

ATA-3

-continued

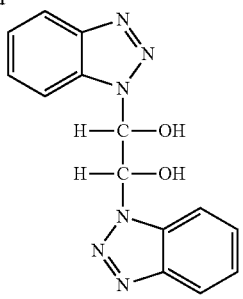

Procedure:

50 ml of Acetic acid and few drops of sulfuric acid were taken in a reaction flask, Benzotriazole was added and heated to 70° C. Aqueous Glyoxal was added to the reaction mixture. The reaction was kept at 25° C. for 24 hours. The solid product was filtered, washed with acetic acid, and dried in vacuum.

Synthesis of BZT-Glyoxylic Acid Derivative

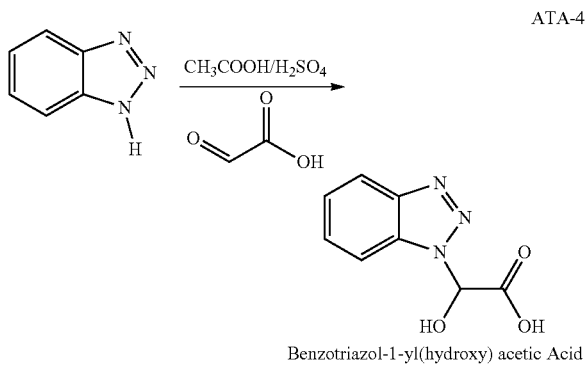

Benzotriazol-1-yl(hydroxy) acetic Acid

Procedure:

Benzotriazole (0.1 mol) was dissolved in acetic acid and few drops of sulfuric acid and heated to 70° C. Glyoxylic acid (0.1 mol) was added to the reaction mixture and heated to 80° C. for 30 minutes and kept at 25° C. for 12 hours. The reaction mixture was cooled at −5° C., and the solid product was filtered, washed with toluene, and dried in vacuum.

In certain aspects of the invention, the ATA reaction products have the structure

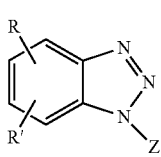

Formula III wherein Z is an alpha hydroxy substituted moiety including an alpha hydroxy substituted lower ($C_1$-$C_4$) alkyl, alpha hydroxy substituted carboxylic ($C_1$-$C_6$) acid, and an alpha hydroxy substituted benzotriazole. Exemplary Z moieties include, methanol, 1-hydroxyethyl, 1-hydroxypropyl, 1 hydroxybutyl, 1 hydroxymethanoic acid, 1-hydroxyethanoic acid, 1-hydroxypropanoic acid, etc. In some instances, Z can be 1,2-dihydroxyethane benzotriazole.

R and R' in Formula III are the same as set forth in Formula I above. Again, it is noted that although the Z moiety is shown at the number 1 nitrogen atom of the triazole ring, it could also be bonded to the number 2 nitrogen. Mixtures of the reaction products may also be formed wherein in some compounds the Z moiety is bonded to the number 1 nitrogen with other compounds having the substituent at the Z nitrogen.

Generally, the AST or mixture thereof is added to a water system such as a cooling water system to inhibit corrosion of metals in contact with the system water. Exemplary metals for which corrosion inhibition is required may include copper based metallurgies such as admiralty brass, or low carbon steel, stainless steel, etc. Generally, the anionically charged functional groups provide: enhanced water solubility across a broad pH spectrum, improved surface bonding capacity, improved chlorine stability, improved chelation capabilities, and improved corrosion protection.

In another embodiment, the ASTs serve as corrosion inhibitors, even in those aqueous systems, such as cooling water systems, in which oxidizing substances are present in order to inhibit microbial growth. For example, the ASTs may be advantageously utilized in systems containing chlorine-containing oxidants, such as, for example, chlorine, chlorine dioxide, sodium chlorite, hypochlorous acid, hypochlorites (e.g., sodium hypochlorite, calcium hypochlorite, etc.), chlorine bleach, etc., nonchlorine-containing oxidants such as acids (e.g., sulfuric acid, nitric acid, etc.), caustics, (e.g., sodium hydroxide, potassium hydroxide, etc.), non-chlorine bleach peroxides (e.g., hydrogen peroxide, sodium peroxide, etc.), ozone, etc.

In other embodiments, the AST may be employed in aqueous systems in which the metallurgy in contact with the system water is treated to provide a protective or passivated film on the metal surface. In such cases, the passivation of iron based metallurgies is typically accomplished through the formation of a cathodic inhibiting calcium phosphate film. Anionic molecules or polymers act as either inhibitors or dispersants of calcium phosphate scale and allow a controlled deposited calcium phosphate film for corrosion control. This deposited film has no negative impacts on industrial assets that rely on heat transfer such as heat exchangers in cooling systems. The AST can facilitate the formation of calcium phosphate inhibiting films on various metallurgies (this includes the various mixed alloys such as admiralty, stainless steel, etc.) including copper, iron, aluminum, etc. The passivating film thus consists of a mixture of inorganic salt and AST on top of a metal oxide layer versus just an azole mechanism. In aggressive waters (grey and or reuse water, high cycle water, RO reject, etc.) that feature increases in conductivity, chlorides, sulfates, TSS total suspended solids, TDS (total dissolved solids), ammonia, oxidizing biocides such a mechanism is desired and forms a more robust field at a much lower dose than typical azoles. Proper passivation of a metal surface will result in decrease metal throw into the aqueous industrial stream.

In some systems adapted to provide passivated films, a treatment comprising an orthophosphate constituent (natural or added as the acid or metal salt) and water soluble polymer is added to system waters that have a calcium ion concentration in excess of about 15 ppm and a pH of about 6.5-9.5. Orthophosphate concentration is on the order of about 6-30 ppm. Typical orthophosphate constituents include phosphoric acid, the sodium orthophosphates, potassium orthophosphates, lithium orthophosphates and ammonium orthophosphates. Also, organic orthophosphates such as those set forth in U.S. Pat. No. 3,510,436 can be mentioned as effective.

The polymers that may be used in order to promote the protective film may include water soluble copolymers or terpolymers based on acrylic acid/hydroxylated alkyl acrylate esters, particularly acryl acid/2 hydroxypropylacrylate copolymers and its salts. Other exemplary copolymers may comprise acrylic/acid/allylhydroxyalkylsulfonate ether polymers such as acrylic acid/allyhydroxypropyl sulfonate ether. In most cases, the orthophosphate component is added in an amount of about 1-30 ppm based on one million parts of the system water. The polymer is present in an amount of about 1-50 ppm, and the AST may be present in an amount of about 1-50 ppm. Techniques pertaining to formation of passivated film may be seen upon review of U.S. Pat. No. 4,303,568.

In other exemplary embodiments, the invention pertains to a process for treating copper based alloys in contact with the aqueous medium of an open cooling system. In some embodiments, a process is provided in which from about 0.1-100 parts by weight of the AST is provided, for every 1 million parts by weight of the aqueous medium. In other embodiments, from about 1-50 ppm may be added with other embodiments adding from 3-5 ppm.

Additional illustrative tests were conducted to assess the efficacy of the ATA reaction products in inhibiting corrosion.

EXAMPLES—SET II ATA

The tests conducted were "Beaker" tests using the protocol reported above under "EXAMPLES SET I".
Results are as follows:

|  | Parent Molecule | | HCHO adduct | | HCHO blend | | CHO—CHO adduct | | CHO—CHO blend | | CHO—COOH adduct | |
|---|---|---|---|---|---|---|---|---|---|---|---|---|
|  | mpy | FC (ppm) | mpy | FC | mpy | FC | mpy | FC | mpy | FC | mpy | FC |
| BZT | 1.121 | 1.7 | 0.445 | 0.8 | 0.631 | 0.8 | 0.51 | 1.45 | 0.268 | 1 | 1.21 | 0.65 |
| Cl-BZT | 0.097 | 1.45 | 0.196 | 0.9 | 0.116 | 2.25 | 0.163 | 2.1 | 0.095 | 0.3 | 0.386 | |
| TTA | 0.887 | 1.55 | 0.358 | 1.95 | 0.184 | 0.45 | 0.237 | 1.35 | 0.116 | 0.75 | 0.17 | 1.05 |
| HCHO-5 | 0.659 | 1.75 | | | | | | | | | | |
| CHO—CHO-6 | 1.099 | 1.05 | | | | | | | | | | |

1. Blends indicate mixtures wherein the alpha hydroxy substituent is located at both the 1 and 2 nitrogen atoms of the azole ring.
2. HCHO adduct=ATA-1
3. CHO—CHO adduct=ATA-3
4. CHO—COOH adduct=ATA-4
5. Formaldehyde by itself.
6. Glyoxal by itself.

The azoles are typically added into cooling towers with other excipients. Information about the formulations is below.

The ANSTs and ATAs can be added with one or more of (a)-(e) below, depending on the water conditions (pH, hardness, cycles of concentration, suspended solids, metallurgy, etc.).

Typically, (e) is included. Typically, (a) and/or (b) is also included.

In the presence of (a) and/or (b) and/or (c), the ability of (d) to passivate a metal is greatly enhanced as it will form a co-film with (a) and/or (b) and/or (c). If (e) is an oxidizer, it will speed up the passivation process by creating a local pH change or formation of an insoluble salt with (c) and/or (d). If (e) is not an oxidizer, the films will still form but at a slower pace.

For enhanced effectiveness of (d), (c) should be present either in the water itself (water sometimes contains salts), or added as a treatment to the water.

A description of (a)-(e) is below:

(a) Salt Inhibitor: polycarboxylic acid (small molecules; oligomers; polymers; examples include polyacrylic acid; maleic acid; polyamino acids such as polyaspartic acid; citrate, succinate; poly epoxy succinic acid; 1-hydroxyethane 1,1-diphosphonic acid (HEDP); 2-Phosphonobutane-1,2,4-tricarboxylic acid (PBTC), DTPMP or diethylenetriamine penta(methylene phosphoric acid), polyphosphonates, and phosphonates. With respect to the phosphonates and polyphosphonates, any phosphoric acid compound with more than 1 phosphate group would be potentially acceptable, typically we use HEDP, PBTC, DTPMP, and U.S. Pat. No. 8,025,840 has a good description. The DCA in U.S. Pat. No. 8,025,840 is a good addition as well, please see columns 2-5 of the patent application. May be present in the cooling water between 0.1 ppm to 100 ppm active preferably between 1-20 ppm.

(b) Dispersant: co-, ter-, and quadpolymers comprising of monomer units with —COOM, —OH, —SO$_3$M, —P)$_3$M, —NH$_2$, —Ar—SO$_3$M, —Ar—COOM, Ar—PO$_3$M, etc. One type of polymer is disclosed in U.S. Pat. Nos. 8,728,324 and 6,444,747. Other types are disclosed in U.S. Pat. No. 4,944,885 (HPSI polymer) and U.S. Pat. No. 6,645,384 (Quadrasperse polymer). Versaflex would also work, and it is a terpolymer with AA, MA, and a sulfonic acid group (—SO$_3$M). May be present in the cooling water between 1 to 200 ppm actives preferably between 1-30 ppm. M is a metal cation salt such as Na, K, Mg, Ca, etc.

(c) Steel Inhibitor: phosphate and/or calcium and/or carbonate. May be present in the cooling water or added to the cooling water with a total concentration of 1-500 ppm preferably between 1-30 ppm for phosphate and 25-250 ppm carbonate. Ca concentrations range between 1 to 10,000 ppm depending on cycles of concentration. Typically we sell various forms of phosphoric acid salt such as oPO$_4$, pPO$_4$, but can use PO$_4$ in water to achieve proper corrosion protection. Ca carbonate typically present in the tower water but in rare examples we may need to add Ca salts or carbonate salts.

(d) Copper Inhibitor: other azoles such as BZT, TTZ, and their respective alkyl and halogenated derivatives. May be present in the cooling water between 1-100 ppm active but preferably between 1-10 ppm.

(e) Microbiological control agent: oxidizers, non-oxidizers, and biodispersants. May be present in the cooling water between 0.1 to 500 ppm but preferably between 0.1 to 20 ppm for oxidizers and non-oxidizers and 1-100 ppm for biodispersants. Oxidizers typically used are bleach, ClO$_2$, peroxide, ozone, and bromine chemistries. Non oxidizers are Kathon, glutaldehyde, Quats of N and P compounds.

It will be apparent to those skilled in the art that many modifications can be made without departing from the invention herein disclosed and described. The invention should not be limited by the disclosure and should be determined only by the attached claims.

We claim:

1. A composition for inhibiting corrosion of metallic surfaces, said composition comprising cooling water from an aqueous system, and an aromatic triazole having an anionic substituent bonded to a nitrogen atom of the triazole (ANST), wherein said ANST has the formula:

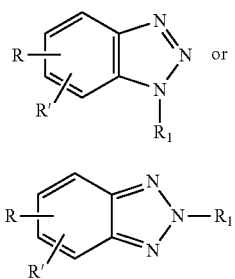

Formula II(a)

or

Formula II(b)

or mixtures of Formulae II(a) and II(b), wherein R and R' are both H, or R is H and R' is methyl, wherein $R_1$ is $R_3Z(n)$ wherein $R_3$ is $CH_2$, Z is phosphonate and n=1.

2. The composition as recited in claim 1, wherein said aqueous system comprises an open recirculating cooling water system, heat exchange system, closed loop system, wastewater system, pulping process system, boiler and other steam generating system, papermaking processes, coke oven gas system, food and beverage processing system, gas scrubbing system, paint detackification system, automotive and tire washing system, reverse osmosis, or membrane system.

3. A composition for inhibiting corrosion of metallic surfaces, said composition comprising cooling water from an aqueous system, and an aromatic triazole having an anionic substituent bonded to a nitrogen atom of the triazole (ANST), wherein said ANST has the formula:

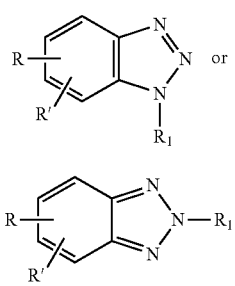

Formula II(a)

or

Formula II(b)

or mixtures of Formulae II(a) and II(b), wherein R and R' are both H, or R is H and R' is methyl, wherein $R_1$ is COOH.

4. The composition as recited in claim 3, wherein said aqueous system comprises an open recirculating cooling water system, heat exchange system, closed loop system, wastewater system, pulping process system, boiler and other steam generating system, papermaking processes, coke oven gas system, food and beverage processing system, gas scrubbing system, paint detackification system, automotive and tire washing system, reverse osmosis, or membrane system.

5. A method of inhibiting corrosion of metal surfaces, wherein said metal surfaces are in contact with an aqueous medium of an aqueous system, the method comprising adding to said aqueous medium an aromatic triazole having an anionic substituent bonded to a nitrogen atom of the triazole (ANST), wherein said ANST has the formula

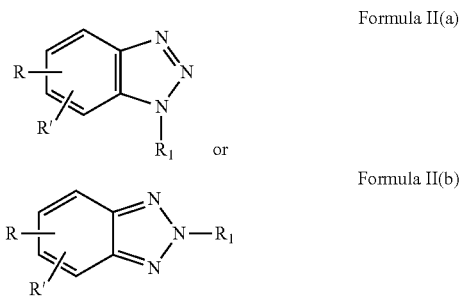

Formula II(a)

or

Formula II(b)

or mixtures of II(a) and II(b),
wherein said aqueous medium comprises cooling water in an open recirculating cooling water system and wherein about 0.1-100 ppm of said ANST is added to said cooling water based upon one million parts of said aqueous medium, wherein said metal surfaces comprise copper, copper alloy, or steel, and wherein corrosion inhibition is obtained by providing for the formation of a protective oxide film on said metal surfaces, and wherein said cooling water system comprises orthophosphate and water soluble polymer therein,
wherein R and R' are both H, or R is H and R' is methyl, and wherein $R_1$ is $R_3Z(n)$ wherein $R_3$ is $CH_2$, Z is phosphonate and n=1.

6. A method of inhibiting corrosion of metal surfaces, wherein said metal surfaces are in contact with an aqueous medium of an aqueous system, the method comprising adding to said aqueous medium an aromatic triazole having an anionic substituent bonded to a nitrogen atom of the triazole (ANST), wherein said ANST has the formula

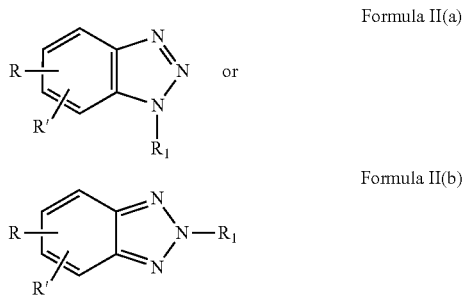

Formula II(a)

or

Formula II(b)

or mixtures of II(a) and II(b),
wherein said aqueous medium comprises cooling water in an open recirculating cooling water system and wherein about 0.1-100 ppm of said ANST is added to said cooling water based upon one million parts of said aqueous medium, wherein said metal surfaces comprise copper, copper alloy, or steel, and wherein corrosion inhibition is obtained by providing for the formation of a protective oxide film on said metal surfaces, and wherein said cooling water system comprises orthophosphate and water soluble polymer therein, wherein R and R' are both H, or R is H and R' is methyl, and wherein $R_1$ is COOH, or $SO_3H$.

* * * * *